(12) United States Patent
Ho et al.

(10) Patent No.: US 11,759,487 B2
(45) Date of Patent: *Sep. 19, 2023

(54) COMPOSITION INCLUDING PROBIOTICS AND METHOD OF INCREASING AMOUNT OF ORAL IMMUNOGLOBULIN A AND INHIBITING ORAL PATHOGENS BY ADMINISTERING THE SAME

(71) Applicant: GLAC BIOTECH CO., LTD., Tainan (TW)

(72) Inventors: Hsieh-Hsun Ho, Tainan (TW); Wen-Yang Lin, Tainan (TW); Yi-Wei Kuo, Tainan (TW); Yen-Yu Huang, Tainan (TW); Jia-Hung Lin, Tainan (TW); Chi-Huei Lin, Tainan (TW); Cheng-Ruei Liu, Tainan (TW); Shu-Hui Chen, Tainan (TW)

(73) Assignee: GLAC BIOTECH CO., LTD., Tainan (TW)

( * ) Notice: Subject to any disclaimer, the term of this patent is extended or adjusted under 35 U.S.C. 154(b) by 0 days.

This patent is subject to a terminal disclaimer.

(21) Appl. No.: 17/511,689

(22) Filed: Oct. 27, 2021

(65) Prior Publication Data
US 2022/0273735 A1    Sep. 1, 2022

(30) Foreign Application Priority Data
Feb. 26, 2021   (TW) ................................ 110107064

(51) Int. Cl.
*A01N 63/00*     (2020.01)
*A61K 35/747*    (2015.01)
*C12N 1/20*      (2006.01)
*A61P 31/04*     (2006.01)
*C12R 1/25*      (2006.01)

(52) U.S. Cl.
CPC ............ *A61K 35/747* (2013.01); *A61P 31/04* (2018.01); *C12N 1/20* (2013.01); *C12R 2001/25* (2021.05)

(58) Field of Classification Search
CPC .................................................... A61K 35/747
See application file for complete search history.

(56) References Cited

U.S. PATENT DOCUMENTS

2018/0206541 A1   7/2018   Hsieh et al.
2021/0401908 A1*  12/2021  Ho ....................... A61K 35/745

FOREIGN PATENT DOCUMENTS

TW     I451871 B    9/2014
TW     I639389 B    11/2018

* cited by examiner

*Primary Examiner* — Albert M Navarro
(74) *Attorney, Agent, or Firm* — THE WEBB LAW FIRM

(57) ABSTRACT

The invention provides a method of increasing an amount of oral immunoglobulin A (IgA) and/or inhibiting oral pathogens in a subject in need thereof, which utilizes a composition including a therapeutically effective amount of probiotics as an effective ingredient. The probiotics include *Lactobacillus plantarum* LPL28, which can efficiently increase the amount of oral IgA and/or inhibit the oral pathogens, and thus have a potential to prevent teeth cavities and/or periodontal diseases.

11 Claims, 11 Drawing Sheets
(4 of 11 Drawing Sheet(s) Filed in Color)
Specification includes a Sequence Listing.

COMPOSITION INCLUDING PROBIOTICS AND METHOD OF INCREASING AMOUNT OF ORAL IMMUNOGLOBULIN A AND INHIBITING ORAL PATHOGENS BY ADMINISTERING THE SAME

CROSS-REFERENCE TO RELATED APPLICATION

A sequence listing is contained in the electronic file titled "2106063_ST25", created on Dec. 8, 2021, with a file size of 1624 bytes is hereby incorporated herein.

This application claims priority to Taiwanese Application Number 110107064 filed Feb. 26, 2021, the disclosure of which is hereby incorporated by reference in its entirety.

BACKGROUND OF THE INVENTION

Field of Invention

The present invention relates to a composition including probiotics and a method of administering the same. Moreover, the present invention relates to a composition including probiotics and the method of increasing an oral mount of immunoglobulin A and inhibiting oral pathogens in a subject in need thereof.

Description of Related Art

There are more than ten thousands bacteria in a human oral cavity. These bacteria digest sugar in the oral cavity to making a substrate for attaching to oral mucus, surfaces of teeth or periodontal tissues, thereby forming tenacious biofilm, and further affecting oral health. Among the bacteria, aerobatic bacteria such as *Streptococcus mutans* prefer to attach on the surfaces of the teeth and secrete acidic substances that erode tooth enamel, resulting in tooth cavities. Moreover, anaerobic bacteria such as *Porphyromonas gingivalis*, *Fusobacterium nucleatum* and *Aggregatibacter actinomycetemcomitans* prefer to attach in the gingival sulcus or the gum boils, where they release toxins that irritate the periodontal tissues, thereby causing inflammation and swelling of periodontal tissues as well as damages of the alveolar bones and the bone tissues. Then, symptoms such as gomphiasis, bad breath and bleeding gums occur.

As one of the openings connecting to the exterior space, the surfaces of an oral cavity is covered by mucus to defense against pathogens, in which immunoglobulin A (IgA) plays an important role in the mucosal immune system and the humoral immunity system. Salivary IgA can maintain an oral ecological balance, prevent pathogens such as respiratory syncytial virus, rotavirus, influenza virus and severe acute respiratory syndrome coronavirus 2 (SARS-CoV-2) from invading respiratory tracts and prevent oral pathogens from attaching to the surfaces of the oral cavity.

Besides immune system, probiotics can also assist human body to defense against oral pathogens. The probiotics can not only compete for nutrients and living spaces against oral pathogens, but also secrete bacteriostatic substances such as bacteriostatic peptides, short chain fatty acid and $H_2O_2$ to inhibit the growth of oral pathogens. In addition, probiotics can also reduce inflammatory symptoms such as swelling, bleeding and ulcer caused causing by the infection of oral pathogens. Moreover, no matter having activities or not, these probiotics and their metabolite (called postbiotics) can also increase the amount of salivary IgA, thereby strengthening oral immunity.

Accordingly, it is necessary to provide a composition including probiotics and a method of using the same to increase the amount of oral IgA and inhibit oral pathogens to strengthen oral immune system and inhibit oral pathogens.

SUMMARY OF THE INVENTION

Accordingly, one aspect of the present invention is to provide a method of increasing an amount of oral immunoglobulin A (IgA) in a subject in need thereof, in which the method includes administering a therapeutically effective amount of a composition including probiotics as an active ingredient, in which the probiotics include specific strains.

In another aspect, the invention provides a method of inhibiting activities of oral pathogens in a subject in need thereof, in which the method includes administering a therapeutically effective amount of a composition including probiotics as an active ingredient, in which the probiotics include the abovementioned specific strains.

In the other aspect, the invention provides a composition for increasing an amount of oral IgA and inhibiting activities of oral pathogens in a subject in need thereof, in which the composition includes a therapeutically effective amount of the abovementioned probiotics as an active ingredient to increase the amount of oral IgA.

According to the aforementioned aspect, the invention provides a method of increasing an amount of oral IgA in a subject in need thereof, in which the method includes administering a therapeutically effective amount of a composition including probiotics as an active ingredient to the subject, in which the probiotics can include but not limited to *Lactobacillus plantarum* LPL28 that is deposited at Bioresource Collection and Research Center (BCRC) under an accession number of BCRC 910536 on Dec. 27, 2011, and also deposited at China General Microbiological Culture Collection Center (CGMCC) (address: Institute of Microbiology, Chinese Academy of Sciences, No. 1 West Beichen Road, Chaoyang District, Beijing 100101, People's Republic of China) under an accession number of CGMCC 17954 on Jun. 18, 2019, in which the viability test has been done on the same day. The deposit has been made under the terms of the Budapest Treaty.

In one embodiment of the invention, the probiotics can further include *L. salivarius* AP-32 and/or *L. paracasei* ET-66. The aforementioned *L. salivarius* AP-32 is deposited in BCRC on Jul. 30, 2009, and China Center for Type Culture Collection (CCTCC) (address: Wuhan University, Wuhan 430072, People's Republic of China) on Apr. 10, 2011 under accession numbers of BCRC 910437 and CCTCC M 2011127, respectively, and the *L. paracasei* ET-66 is deposited in BCRC on Nov. 3, 2016 and deposited in China General Microbiological Culture Collection Center (CGMCC) (address: Institute of Microbiology, Chinese Academy of Sciences, Datun Road, Chaoyang District, Beijing 100101, People's Republic of China) on Dec. 29, 2016 under accession numbers of BCRC 910752 and CGMCC 13514, respectively. The viability test has been done on Apr. 19, 2011 for *L. salivarius* AP-32 and on Jan. 6, 2017 for *L. paracasei* ET-66. The deposits have been made under the terms of the Budapest Treaty.

In one embodiment of the invention, the composition can be a food composition or an oral topical composition, for example.

In one embodiment of the invention, the food composition can be a dairy product, a non-dairy beverage or an oral cleansing food, for example.

In one embodiment of the invention, the oral topical composition can be an oral care composition or a breath freshening composition, for example.

According to the aforementioned aspect, the invention further provides a method of inhibiting activities of oral pathogens in a subject in need thereof, in which the method includes administering a therapeutically effective amount of a composition including probiotics as an active ingredient of the composition, for example, to inhibit a growth of the oral pathogens, and the probiotics can include *L. plantarum* LPL28 (BCRC 910536 and CGMCC 17954).

In one embodiment of the invention, the probiotics can further include *L. salivarius* AP-32 (BCRC 910437 and CCTCC M 2011127) and/or *L. paracasei* ET-66 (BCRC 910752 and CGMCC 13514).

In one embodiment of the invention, the oral pathogens include *Streptococcus mutans* and/or periodontal pathogens.

In one embodiment of the invention, the periodontal pathogens include *Porphyromonas gingivalis, Fusobacterium nucleatum* and *Aggregatibacter actinomycetemcomitans*.

In one embodiment of the invention, the composition can be a food composition or an oral topical composition.

According to the aforementioned aspect, the invention further provides a composition for increasing an amount of oral IgA and inhibiting oral pathogens in a subject in need thereof. The composition comprises therapeutically effective amounts of probiotics as an active ingredient, in which the probiotics can be consisted of *L. plantarum* LPL28 (BCRC 910536 and CGMCC 17954), *L. salivarius* AP-32 (BCRC 910437 and CCTCC M 2011127) and *L. paracasei* ET-66 (BCRC 910753 and CGMCC 13514).

By applying the abovementioned composition, the amount of salivary IgA can increase effectively and/or the growth of oral pathogens can be inhibited effectively, thereby increasing immunity in an oral cavity and maintaining oral health.

BRIEF DESCRIPTION OF THE DRAWINGS

The patent or application file contains at least one drawing executed in color. Copies of this patent or patent application publication with color drawings will be provided by Office upon request and payment of the necessary fee. The invention can be more fully understood by reading the following detailed description of the embodiment, with reference made to the accompanying drawings as follows:

(FIG. 4C) and *Lactobacillus* spp. (FIG. 4D) in percentage, respectively, according to an embodiment of the present invention.

DESCRIPTION OF THE INVENTION

Figure 1:
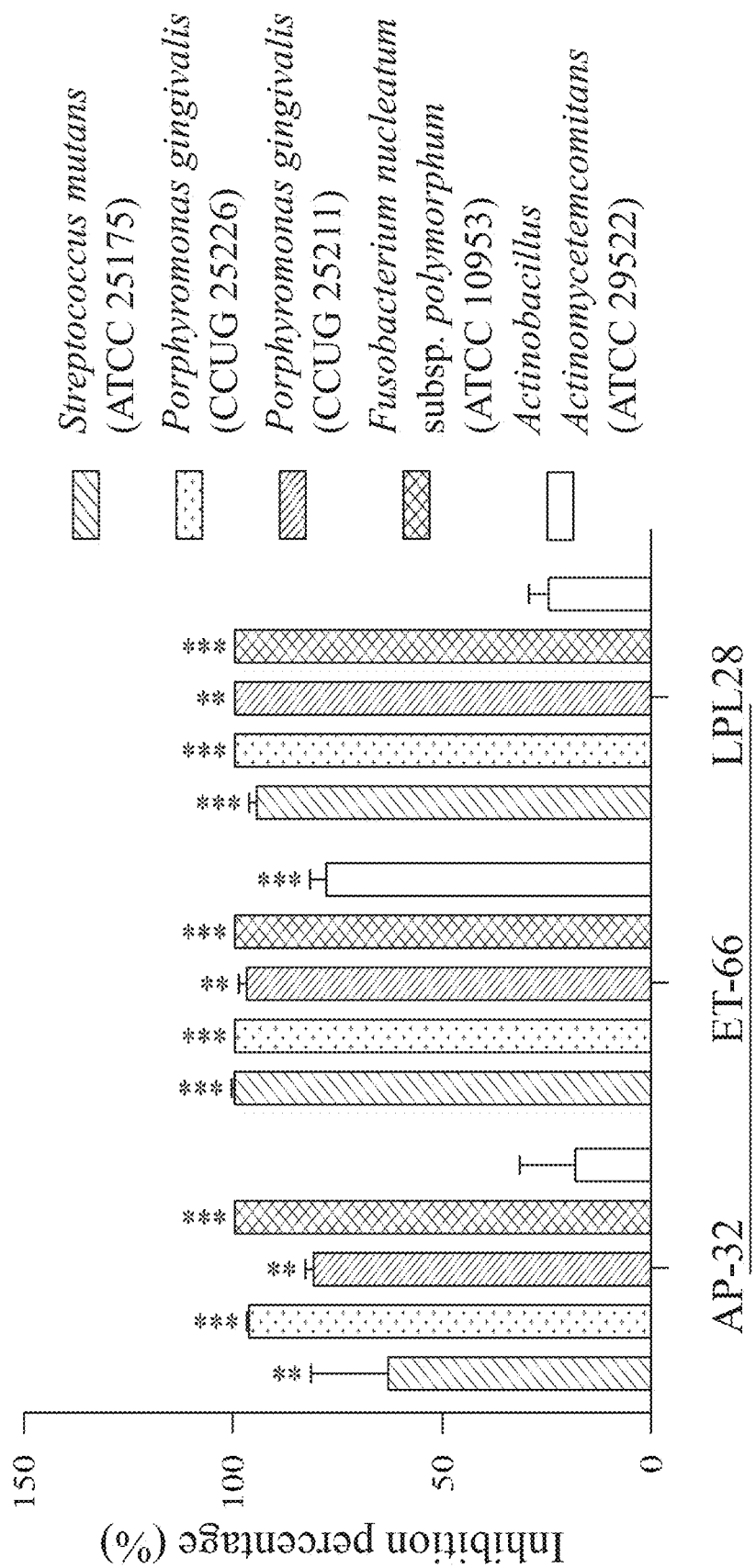
FIG. 1 is a bar chart showing the inhibition percentages of the single-strain postbiotics of different probiotics against different oral pathogens in vitro according to an embodiment of the present invention.
Figure 2A:
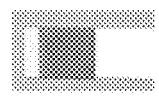
FIGS. 2A to 2E are the test strips measuring the secreting amounts of $H_2O_2$ of the strains AP-32 (FIG. 2A), ET-66 (FIG. 2B), LPL28 (FIG. 2C), three-mixed strains (FIG. 2D) and the colorimeter (FIG. 2E), respectively, according to an embodiment of the present invention.
Figure 2B:
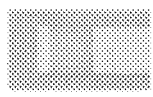
Figure 2C:
Figure 2D:
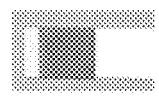
Figure 2E:
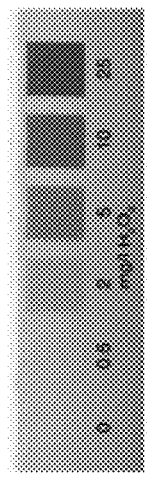

Accordingly, one aspect of the present invention is to provide a method of increasing an amount of oral immunoglobulin A (IgA) in a subject in need thereof, in which the method includes administering a therapeutically effective amount of a composition including probiotics as an active ingredient to the subject. The aforementioned probiotics can include but not limited to *Lactobacillus plantarum*. In one embodiment, the *L. plantarum* is the strain LPL28 deposited at Bioresource Collection and Research Center (BCRC) (address: No. 331 on Shih-Pin Road, Hsinchu 30062, Taiwan) under an accession number of BCRC 910536 on Dec. 27, 2011. Besides, *L. plantarum* LPL28 has also been deposited at China General Microbiological Culture Collection Center (CGMCC) (address: Institute of Microbiology, Chinese Academy of Sciences, No. 1 West Beichen Road, Chaoyang District, Beijing 100101, People's Republic of China) under an accession number of CGMCC 17954 on Jun. 18, 2019, in which the date of the viability test has been done on the same day. The deposit has been made under the terms of the Budapest Treaty.

In addition, the abovementioned probiotics can selectively include *L. salivarius* and/or *L. paracasei*. In one embodiment, the *L. salivarius* is referred in Taiwan patent Number TW I451871B, and is deposited in BCRC on Jul. 30, 2009 under an accession number of BCRC 910437. In one embodiment, *L. paracasei* ET-66 is referred in Taiwan patent Number TW I639389B, and is deposited in BCRC on Nov. 3, 2016 under an accession number of BCRC 910753. In one embodiment, the probiotics is consisted of *L. plantarum* LPL28, *L. salivarius* AP-32 and *L. paracasei* ET-66.

In addition, the *L. salivarius* AP-32 is also deposited in China Center for Type Culture Collection (CCTCC) (address: College of Life Sciences, Wuhan University, Wuhan 430072) on Apr. 10, 2011 under an accession number of CCTCC M 2011127. The abovementioned *L. paracasei* ET-66 is also deposited in China General Microbiological Culture Collection Center (CGMCC) (address: Institute of Microbiology, Chinese Academy of Sciences, Datun Road, Chaoyang District, Beijing 100101, People's Republic of China) on Dec. 29, 2016 under an accession number CGMCC 13514. The viability test has been done on Apr. 19, 2011 for *L. salivarius* AP-32 and on Jan. 6, 2017 for *L. paracasei* ET-66. The deposits have been made under the terms of the Budapest Treaty.

The aforementioned probiotics was subjected to a fermentation step with a fermenting medium to obtain a fermented product, in which the types of the fermenting medium are not limited and can be a commercial bacterial medium, for example, and the fermented product includes live probiotic cells. The fermentation step can be a single-strain fermentation step using a single strain of probiotic to obtain a single-strain fermented product, for example. In one embodiment, the fermentation step can be a multiple mixed-strain fermentation step using multiple strains of probiotics to obtain a multiple mixed-strain fermented product, for example, in which the multiple strains of probiotics can be selected from a group consisting of *L. plantarum* LPL28, *L. salivarius* AP-32, *L. paracasei* ET-66 and any combination thereof. In one embodiment, the fermentation step can be a three mixed-strain fermentation step performed on *L. plantarum* LPL28, *L. salivarius* AP-32, and *L. paracasei* ET-66 simultaneously to obtain a three mixed-strain fermented product, for example.

Next, the fermented product (e.g., single-strain fermented product or multiple mixed-strain fermented product) is subjected to a post-treatment to obtain postbiotics (e.g., the single-strain postbiotic or the multiple mixed-strain postbiotics), in which the postbiotics include the bacterial cells and their metabolites generated from the medium digested by bacterial cells. Methods of the abovementioned post-treatment can include but not limited to a heat-kill step and/or a solid-liquid separation step. The aforementioned heat-kill step can inhibit bacterial activities, thereby forming inactive bacterial cells, and the solid-liquid separation step can remove the active bacterial cells and/or the inactive bacterial cells. In one embodiment, the aforementioned active ingredient can be selected from a group consisting of the active bacterial cells, the inactive bacterial cells, the postbiotics of probiotics and any combination thereof. In one embodiment, the heat-kill step can be performed with a moist wet kill method (e.g., an autoclave method, a microwave heat method or a water bath method) and/or a dry heat-kill method, for example. In one embodiment, the solid-liquid separation step can be performed with a centrifuge method and/or a filter method.

The abovementioned probiotics can increase the amount of oral IgA and inhibit oral pathogens effectively. IgA can be found in oral mucus and salivary and is related to oral health. Thus, increasing the amount of salivary IgA can reduce the sicknesses caused by oral pathogens. "Inhibiting oral pathogens" herein indicates to inhibit the growth of oral pathogens, for example.

The aforementioned "oral pathogens" can be microorganisms effecting oral health, in which the oral pathogens can include but not limited to caries-causing bacteria and/or periodontal pathogens. The aforementioned caries-causing bacteria can include *Streptococcus mutans*, and the periodontal pathogen can include *Porphyromonas gingivalis, Fusobacterium nucleatum* and *Aggregatibacter actinomycetemcomitans*. In addition, *P. gingivalis, F. nucleatum* and *A. actinomycetemcomitans* can produce sulfide, thereby causing bad breath. Besides effecting oral health, oral pathogens are also related to other diseases apart from oral diseases. For example, *F. nucleatum* is closely related to colon cancers, *A. actinomycetemcomitans* is closely related to colorectal cancers, and the amounts of *Porphyromonas gingivalis* and *A. actinomycetemcomitans* have been found to be positively correlated to the incidence of pancreatic cancer. Thus, inhibiting oral pathogen growth can not only maintain oral health, but also reduce the incidence of the abovementioned disease.

The routes of administration are not specifically limited when applying the abovementioned composition, which can be administered through mouth and/or absorb orally. The routes of administration can be adjusted depending on actual needs and dosage form of the composition. The effective dose of the abovementioned composition can be adjusted flexibly depending on actual needs. In one embodiment, an effective dose of the probiotics is higher than $10^6$ CFU/g, but $10^7$ CFU/g to $10^{11}$ CFU/g is better.

In one embodiment, the abovementioned composition can selectively include a food- or a drug-acceptable excipient, diluent or carrier, etc. In one embodiment, the composition can be a food composition or an topically oral composition, in which the food composition can be a dairy product (e.g., yogurt, cheese, milk powder of fermented milk-made drink), non-dairy drinks (e.g., tea, coffee or health drink) or teeth-cleaning food (e.g., chewing gum, a lozenge, fudge and dried meat for pets), and the topically oral composition can be an oral care composition (e.g., toothpaste, dental floss, mouthwash, toothpowder, a denture cleaner or oral cream), a breath freshening composition (e.g., a breath freshener) or other compositions (e.g., a teeth whitening agent).

The in vivo experiments have proved that the abovementioned *Lactobacillus plantarum* LPL28 mixed with other bacterial species (e.g., *L. salivarius* AP-32 and *L. paracasei* ET-66) can effectively increase the amount of oral IgA and inhibit the oral pathogens, implying that the abovementioned probiotics has the potential to decrease teeth cavities and/or periodontal diseases, thereby maintaining the oral health.

To add, in vivo experiments have shown that the three mixed-strain fermented product is able to secrete more $H_2O_2$ compared to the individual single-strain fermented product. Moreover, the three mixed-strain postbiotic can increase the amounts of oral IgA in comparison with the individual single-strain postbiotic, indicating that the three mixed-strain fermented product and/or three mixed-strain postbiotics consisting of *L. plantarum* LPL28, *L. salivarius* AP-32 and *L. paracasei* ET-66 are more beneficial for oral health in comparison with the single-strain fermented product and/or single-strain postbiotic of *L. plantarum* LPL28.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the followed claims.

Example 1

Isolation and Preservation of *Lactobacillus plantarum* LPL28 and its Microbiological Properties

*Lactobacillus plantarum* LPL28 (abbreviated as LPL28) was a strain isolated from miso. After separation, the strain LPL28 was preserved in MRS broth (Difco) (Becton, Dickinson and Company, Singapore) with 20% glycerol under −80° C. The strain LPL28 was inoculated in the MRS broth with 0.05 wt % cysteine at 37° C. for 24 hours, and was sub-cultured with the same method again, for ensuring that the strain LPL28 had a better activity.

After activated, the strain LPL28 was spread on the MRS agar medium and was incubated at 37° C. for about 48 hours to grow colonies. The morphology of the activated strain LPL28 was observed and the results were recorded in Table 1.

TABLE 1

| Morphology of the strain | 1. Gram-positive and facultative heterofermentative. |
|---|---|
| | 2. The colony was and solid round white cultured in |

TABLE 1-continued

| | |
|---|---|
| LPL28 | the MRS medium. The cell had a short rod-like shape and the ends of the cell were square. The cells often appeared in pairs or short-chains. |

Then, the strain LPL28 was identified with a microbial identification kit (API 50 CHL, made by bioMerieux, Marcy-l'Étoile, France), and the results were shown in Table 2, in which "+" indicated a positive reaction, "−" indicated a negative reaction, and "?" indicated a weak reaction. According to the results shown in Table 2, the biochemical properties of the strain LPL28 were similar to that of *L. plantarum*, and thus the strain LPL28 was determined as *L. plantarum*.

TABLE 2

| Test items | LPL28 | Test items | LPL28 | Test items | LPL28 |
|---|---|---|---|---|---|
| Glycerol | − | D-mannitol | + | D-raffinose | + |
| Erythritol | − | D-sorbitol | + | Amidon | − |
| D-arabinose. | − | Methyl-alpha-D-mannopyranoside | ? | Glycogen | − |
| L-arabinose | − | Methyl-alpha-D-glucopyranoside | − | Xylitol | − |
| D-ribose | ? | N-acetylglucosamine | + | Gentiobiose | + |
| D-xylose | − | Amygdalin | + | D-turanose | − |
| L-xylose | − | Arbutin | + | D-lyxose | − |
| D-xylose | − | Esculin ferric citrate | + | D-tagatose | − |
| Methyl-beta-D-xylopyranoside | − | Salicin | + | D-fucose | − |
| D-galactose | + | D-cellobiose | + | L-fucose | − |
| D-glucose | + | D-maltose | + | D-arabitol | − |
| D-fructose | + | D-lactose | + | L-arabitol | − |
| D-mannose | + | D-melibiose | + | Potassium gluconate | ? |
| L-sorbose | − | D-saccharose | + | Potassium 2-ketogluconate | − |
| L-rhamnose | − | D-trehalose | + | Potassium 5-ketogluconate | − |
| Dulcitol | − | Inulin | − | | |
| Inositol | − | D-melezitose | + | | |

Next, a RNA purification and a reverse transcription-PCR (RT-PCR) were performed to obtain the 16S rDNA of the strain LPL28, followed by a PCR performed with primer pairs having sequences shown in SEQ ID NOs. 1 and 2 to obtaining an amplification product of 145 bp with a sequence shown in SEQ ID NO. 3. The strain LPL28 was identified as *L. plantarum* by analyzing with a local alignment search tool (BLAST). The isolated strain was deposited at BCRC under an accession number of BCRC 910536 as well as CGMCC under an accession number of CGMCC 17954.

Example 2

In Vitro Evaluation of Inhibition Activity of *L. plantarum* LPL28 Against Oral Pathogens The inhibition activities of probiotics against oral pathogens was evaluated by a double layer plate method, in which the test probiotic strains were listed in Table 3, and examples of the oral pathogens were listed in Table 4. It was worth noting that the strain LGG was a commercial probiotic strain known to inhibit *Streptococcus mutans* and was the positive control herein.

TABLE 3

| Species | Strain | Provider or accession number |
|---|---|---|
| *L. salivarius* subsp. *salicinius* | L-1 | glac Biotech |
| *L. plantarum* | LPL28 | glac Biotech |
| *L. helveticus* | L-75 | glac Biotech |
| *L. rhamnosus* | L-35 | glac Biotech |
| | LGG | ATCC 53103 |
| *Lactococcus lactis* subsp. *lactis* | L-87 | glac Biotech |
| *L. johnsonii* | L-3 | glac Biotech |
| *L. reuteri* | L321 | glac Biotech |
| | L-4 | glac Biotech |
| | L-21 | glac Biotech |

TABLE 3-continued

| Species | Strain | Provider or accession number |
|---|---|---|
| *Bifidobacterium lactis* | BB-12 | DSM 15954 |
| *Streptococcus thermophilus* | L-37 | glac Biotech |
| | L-102 | glac Biotech |
| *L. acidophilus* | LA-5 | DSM 13241 |

ATCC: American Type Culture Collection, 10801 University Boulevard, Manassas, Virginia 20110-2209.
DSM: Leibniz-Institut DSMZ-Deutsche Sammlung von Mikroorganismen und Zellkulturen GmbH, Inhoffenstr. 7B, Braunschweig 38124, German.

TABLE 4

| Species | Accession number |
|---|---|
| *Streptococcus mutans* | ATCC 25175 (i.e., BCRC 10793) |
| *Porphyromonas gingivalis* | CCUG 25226 (i.e., BCRC 17689) |
| | CCUG 25211 (i.e., BCRC 17688) |
| *Fusobacterium nucleatum* subsp. *polymorphum* | ATCC 10953 (i.e., BCRC 17679) |
| *Actinobacillus actinomycetemcomitans* | ATCC 29522 (i.e., BCRC 14405) |

CCUG: Culture Collection University of Gothenburg, Gothenburg, Kingdom of Sweden.

First, the MRS broth was used to culture the probiotic strains shown in Table 3 to obtain liquid cultures of probiotics. Moreover, tryptic soy broth (TSB) was used to culture *S. mutans*, *P. gingivalis* and *F. nucleatum* subsp. *polymorphum* while brain heart infusion (BHI) broth was used to culture *A. actinomycetemcomitans* to obtain liquid cultures of pathogens. The amounts of cells in the liquid cultures of probiotics and the liquid cultures of pathogens were adjusted to $1\times10^9$ cfu/g and $1\times10^7$ cfu/g to $1\times10^9$ cfu/g, respectively.

The liquid cultures of the probiotic strains were respectively streaked on a first agar medium in lines, followed by incubation under 37° C. for about 48 hours in an anaerobic condition to obtain probiotic bands having a width of 2 cm. The aforementioned first agar culture plate was prepared by the MRS medium.

Next, the 45° C. second layer agar medium was added on the first agar medium. After the second layer agar medium was cooled and solidified, the liquid cultures of pathogens of each oral pathogen strains were spread on the second layer agar medium, followed by an incubation under 37° C. for 48 hours, in which the second layer agar medium was prepared by TSB medium for *S. mutans*, *P. gingivalis* and *F. nucleatum* subsp. *polymorphum* or BHI medium for *A. actinomycetemcomitans*. Inhibition bands would form on both sides of the probiotic bands of the probiotic strain on the second layer agar medium when the probiotic strain had an inhibition activity. The inhibition activity of the probiotic strain could be quantified by the width of the bacteriostatic band, in which a the probiotic strain having the inhibition band with a width that was less than 1 cm, 1 cm to 2 cm, 2 cm to 3 cm or more than 3 cm received an inhibition score of 0, 1, 2 or 3, respectively.

The inhibition scores of the probiotic strains against different oral pathogens and the averages were recorded in Table 5. As shown in Table 5, the inhibition score of the strain LPL28 was higher than that of other probiotic strains and was even higher than that of the positive control strain LGG, indicating that the activated cells of the strain LPL28 had an excellent inhibition activity.

Example 3

In Vivo Evaluation of Inhibition Activities of Postbiotics of *L. plantarum* LPL28 Against Oral Pathogens The probiotic strains LPL28, *L. salivarius* AP-32 and *L. paracasei* ET-66 were respectively subjected to a single-strain fermentation step for obtaining single-strain fermented products, in which the single-strain fermentation step was performed under 37° C. for 48 hours with the MRS medium. *L. salivarius* AP-32 (accession number: BCRC 910437 and CCTCC M 2011127, abbreviated as strain AP-32) and *L. paracasei* ET-66 (accession number: BCRC 910753 and CGMCC 13514, abbreviated as strain ET-66) were described in the Taiwan Patent No. TW I639389B and would not be elaborated herein.

Next, the single-strain fermented products were subjected to a post-treatment to obtain single-strain postbiotics, in which the post-treatment included a heat-kill step and a centrifuge step. The aforementioned heat-kill step was performed by a water bath at 100° C. such that the cells of the single-strain fermented products lost their activities. The aforementioned centrifuge step was performed with a centrifugation speed of 4000 rpm for 10 minute, in which the separated supernatants included the single-strain postbiotics.

The postbiotic cultures were prepared respectively by adding 100 µL of the single-strain postbiotics and subsequently 100 µL of the liquid cultures of pathogens with $10^6$ CFU/mL pathogens in 4.8 mL of the TSB medium for *S. mutans*, *P. gingivalis* and *F. nucleatum* subsp. *polymorphum* or the BHI medium for *A. actinomycetemcomitans*. A control culture was prepared with the same method to prepare the postbiotic cultures without adding the postbiotics.

The postbiotic cultures and the control culture were respectively serial diluted and spread on the TSB agar medium (*S. mutans*, *P. gingivalis* and *F. nucleatum* subsp. *polymorphum*) or the BHI agar medium (*A. actinomycetemcomitans*), followed by an incubation at 37° C. for 48 hours. Then, numbers of colonies were counted, and the numbers of colonies of the postbiotic cultures were divided by numbers of colonies of the control cultures and multiplied by 100% to obtain the survival percentage, and the inhibition

TABLE 5

| | | | Probiotic strains | | | | | |
|---|---|---|---|---|---|---|---|---|
| Inhibition scores | | | LPL28 | L-1 | LGG | L-75 | L-35 | L-87 | L-3 |
| Oral pathogens | *S. mutans* | | 3 | 3 | 3 | 2 | 2 | 3 | 3 |
| | *P. gingivalis* | CCUG 25226 | 3 | 3 | 2 | 2 | 2 | 2 | 1 |
| | | CCUG 25211 | 3 | 2 | 2 | 2 | 2 | 2 | 1 |
| | *F. nucleatum* subsp. *polymorphum* | | 3 | 3 | 2 | 2 | 2 | 2 | 2 |
| | *A. actinomycetemcomitans* | | 2 | 2 | 3 | 1 | 1 | 0 | 0 |
| | Average | | 2.8 | 2.6 | 2.4 | 1.8 | 1.8 | 1.8 | 1.4 |

| | | | Probiotic strains | | | | | |
|---|---|---|---|---|---|---|---|---|
| Inhibition scores | | | LA-5 | L321 | L-4 | BB-12 | L-37 | L-21 | L-102 |
| Oral pathogens | *S. mutans* | | 0 | 1 | 0 | 3 | 2 | 0 | 0 |
| | *P. gingivalis* | CCUG 25226 | 1 | 1 | 2 | 0 | 1 | 1 | 0 |
| | | CCUG 25211 | 1 | 1 | 1 | 0 | 1 | 1 | 0 |
| | *F. nucleatum* subsp. *polymorphum* | | 2 | 1 | 2 | 0 | 0 | 2 | 0 |
| | *A. actinomycetemcomitans* | | 0 | 2 | 0 | 2 | 0 | 0 | 0 |
| | Average | | 0.8 | 1.2 | 1 | 1 | 0.8 | 0.8 | 0 | percentage were obtained by subtracted the survival percentage from 100%. Thus, the inhibition percentage of the control culture was 0%.

FIG. 1 was a bar chart showing the inhibition percentages of the single-strain postbiotics of different probiotics against different oral pathogens in vitro according to an embodiment of the present invention, in which the x-axis represented the postbiotics of the probiotic strains, the y-axis represented the inhibition percentage, and symbols "*", "" and "*" represented a statistically significant difference in the inhibition percentages compared to control culture ($p<0.05$, $p<0.01$ and $p<0.001$, respectively) analyzed by Student t-test.

As shown in FIG. 1, the inhibition percentages of the single-strain postbiotics of the strains LPL28, AP-32 and ET-66 against the oral pathogens were higher compared to that of the control cultures without postbiotics, indicating that the single-strain postbiotics of the strains LPL28, AP-32 and ET-66 had excellent inhibition activities.

Example 4

Measurement of Secreting Amount $H_2O_2$ of Different Probiotic Strains $H_2O_2$ could inhibit the growth of bacteria, and could whiten teeth. Thus, the inhibition activities of by probiotic strains could be evaluated by measuring the secreting amounts of $H_2O_2$. First, the strains AP-32, ET-66 and LPL28 were subjected to the aforementioned single-strain fermentation step with the MRS medium, whereas a mixture of the strains AP-32, ET-66 and LPL28 were subjected to a three mixed-strain fermentation step with the MRS medium, thereby obtaining single-strain fermented products of each strains and a three mixed-strain fermented product, respectively. The conditions of the three mixed-strain fermentation step were same as the single-strain fermentation step except that the amounts of inoculated strains were different. The total amounts of the cells of the single-strain fermented products and that of the three mixed-strain fermented product were the same (about $10^9$ CFU/mL), in which the amount ratio of the cells of the strains AP-32, ET-66 and LPL28 of the three mixed-strain fermented product were 1:1:1. 0.1 mL of the single-strain fermented products and 0.1 mL of the three mixed-strain fermented product were centrifuged at a centrifugation speed of 4500 rpm for 5 minutes to obtain pellets. Then, the pellets were redissolved by 4.9 mL piperazine-N,N'-bis (2-ethanesulfonic acid) (PIPES) buffer (100 mM), followed by a centrifugation at a centrifugation speed of 220 rpm for 5 hours to obtain PIPES cultures. Next, the PIPES cultures were centrifuged at a centrifugation speed of 4500 rpm, and 10 μL of the obtained supernatants were added to test strips for $H_2O_2$ (Merck Millipore, Darmstadt, Germany), and the color changes of the test strips were observed 10 seconds later. The $H_2O_2$ concentration could be obtained by comparing the colors of the test strips to that of a colorimeter. The results were recorded in FIGS. 2A to 2E.

FIGS. 2A to 2E were the test strips measuring the secreting amounts of $H_2O_2$ of the strains AP-32 (FIG. 2A), ET-66 (FIG. 2B), LPL28 (FIG. 2C), three mixed strains (FIG. 2D) and the colorimeter (FIG. 2E), respectively, according to another embodiment of the present invention. As shown in FIGS. 2A to 2D, the PIPES cultures of the single-strain fermented products of the strains AP-32, ET-66 and LPL28 included amounts of $H_2O_2$ of 5 mg/L, 0 mg/L and 2 mg/L, respectively, and the amounts of $H_2O_2$ of the PIPES culture of the three mixed-strain fermented product was 10 mg/L, which was higher than the sum of the amounts of $H_2O_2$ of the single-strain fermented products, indicating that the three mixed-strain fermented product obtained by performing the three mixed-strain fermentation step on the strains AP-32, ET-66 and LPL28 at the same time had a higher secreting amounts of $H_2O_2$ compared to the single-strain fermented product obtained by respectively performing the single-strain fermentation step on the strains AP-32, ET-66 and LPL28.

Example 5

In Vitro Evaluation of Inhibition Activities of Three Mixed-Strain Postbiotic Lozenge Against Oral Pathogens The placebo lozenge and the three mixed-strain postbiotic lozenge were prepared. The ingredient of the abovementioned placebo lozenge contained food additives such as a sweetener (e.g., D-sorbitol, erythritol and sucralose), fructooligosaccharides, lactose, flavors, magnesium stearate and silicon dioxide, in which the amounts the food additives could be adjusted depending on actual needs and regulatory requirements. The abovementioned food additives were known ingredient and could be adjusted arbitrarily depending on actual needs without influencing the evaluation of the inhibition activities and thus would not be elaborated herein. Besides, the ingredient of the three mixed-strain postbiotic lozenge contained the food additives of the placebo lozenge and the three mixed-strain postbiotic. The three mixed-strain postbiotic was obtained by performing the abovementioned three mixed-strain fermentation step and the abovementioned post-treatment, in which the three mixed-strain postbiotic contained $1\times10^9$ CFU/mL cells, and the amount of the three mixed-strain postbiotic in the three mixed-strain postbiotic lozenge was 50 mg/g.

The lozenge cultures of the placebo lozenge and the three mixed-strain postbiotic lozenge were prepared by adding 100 μL liquid cultures of pathogens into 4.8 mL TSB medium (*S. mutans, P. gingivalis* and *F. nucleatum* subsp. *polymorphum*) or the BHI medium (*A. actinomycetemcomitans*), and then one placebo lozenge or one three mixed-strain postbiotic lozenge were added, followed by an incubation at 37° C. for 20 hours (for *S. mutans*) or 4 days (for *P. gingivalis, F. nucleatum* subsp. *polymorphum* and *A. actinomycetemcomitans*). In addition, the control culture was prepared, in which the preparation method was same as that of preparing the abovementioned lozenge cultures without adding the lozenges. Then, the inhibition percentages were calculated with the method showed in EXAMPLE 3, and the results were recorded in FIG. 3.

Figure 3:
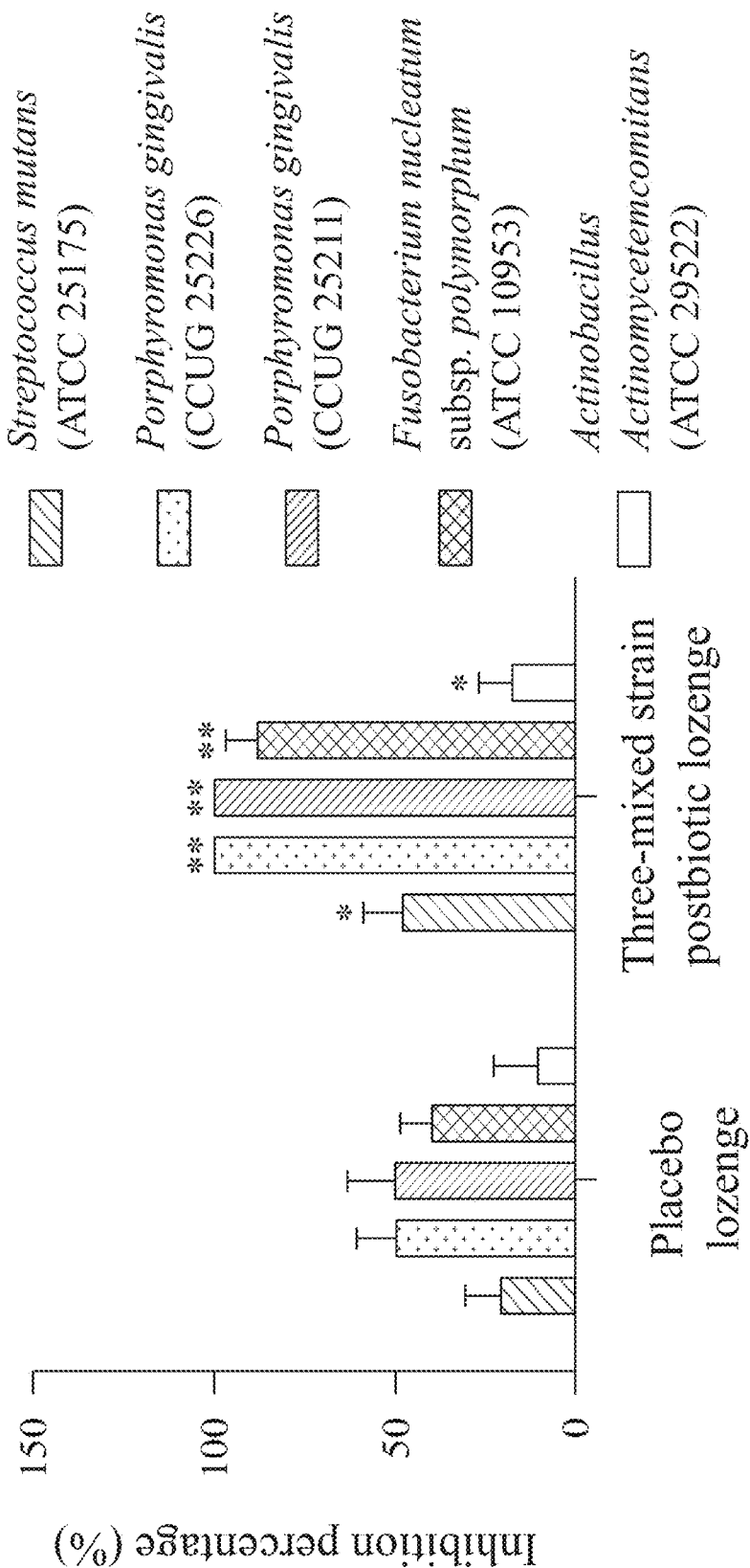
FIG. 3 is a bar chart showing the inhibition percentage of the three mixed-strain postbiotics lozenge against different oral pathogens according to an embodiment of the present invention.

FIG. 3 was a bar chart showing the inhibition percentage of the three mixed-strain postbiotic lozenge against different oral pathogens according to an embodiment of the present invention, in which the x-axis represented the groups, the y-axis represented the inhibition percentage, and symbols "*" and "**" represented statistically significant differences from the inhibition percentages of the placebo lozenge ($p<0.05$, $p<0.01$, respectively) analyzed by Student t-test. As shown in FIG. 3, the inhibition percentage of the three mixed-strain postbiotic lozenge against the oral pathogens was higher than that of the placebo lozenge, indicating that the three mixed-strain postbiotic lozenge could inhibit oral pathogens effectively.

Example 6

In Vivo Evaluation of Inhibition Activities of Three Mixed-Strain Probiotic Lozenge Against Oral Pathogens in Oral and/or Benefits on Maintaining Gastrointestinal (GI) Health The three mixed-strain probiotic lozenge and probiotic lozenges of strains AP-32, ET-66, LPL28 were prepared by the cells obtained in EXAMPLE 4 after centrifuging, in which the probiotic lozenges contained the additives of the placebo lozenge and the aforementioned cells, and the total amount of the cells was 50 mg/g in the probiotic lozenges.

The aforementioned placebo lozenge and the three mixed-strain probiotic lozenge were respectively administered to subjects for 4 weeks by placing one of each in the subjects' mouths without chewing respectively in the morning, the noon and the night. The aforementioned subjects were 20-to-40-year-old health adults who had no systemic diseases and did not smoke. Moreover, each of the subjects had about $10^5$ cells of S. mutans in the saliva. Noted that the weight of each lozenge was about 10 g, and the lozenge could slowly dissolve in a mouth for about 10 minutes but the time varied among individuals depending on factors such as the amounts of saliva and the body temperatures of the subjects.

The oral tissue samples were obtained before administering the lozenge, 2 weeks and 4 weeks after administering the lozenge by swabbing the labial surface and the and the buccal surface of the teeth with cotton swabs. Next, the oral tissue samples were inoculated evenly in 5 mL TBS medium containing 50% glycerol to obtain oral bacterial samples. Then, the oral bacterial samples were incubated at 37° C. for 2 days under the corresponding cultural conditions according to the targets to be detected. In details, the corresponding cultural conditions contained the specific cultural medium and the oxygen condition. The oral bacterial samples were incubated with a plate count agar medium under an aerobic condition to culture oral aerobic bacteria. The oral bacterial samples were incubated with a mitis salivarius agar (MSBA) medium under a facultative anaerobe condition to incubate S. mutans. The oral bacterial samples were incubated with a cysteine MRS agar medium under an anaerobic condition or a facultative anaerobe condition to incubate Bifidobacterium spp. or Lactobacillus spp. The cell amounts of each strain were shown in FIGS. 4A to 4D.

FIGS. 4A to 4D were bar charts showing the changes in the numbers of oral aerobic bacteria (FIG. 4A), S. mutans (FIG. 4B), Bifidobacterium spp. (FIG. 4C) and Lactobacillus spp. (FIG. 4D) in percentage, respectively, according to an embodiment of the present invention, in which the x-axis represented the types of the lozenges and the method to administer the lozenges, the y-axis represented the numbers of the bacteria in percentage taking the numbers of the oral bacteria before the administration as 100%, the symbols "*", "" and "*" represented statistically significant differences from the numbers of the bacteria after administrating placebo lozenges ($p<0.05$, $p<0.01$ and $p<0.001$, respectively) (n=25) analyzed by Student t-test, and symbols "#", "##" and "###" represented statistically significant differences from the numbers of the bacteria before the administration ($p<0.05$, $p<0.01$ and $p<0.001$, respectively) (n=25) analyzed by Student t-test.

Figure 4A:
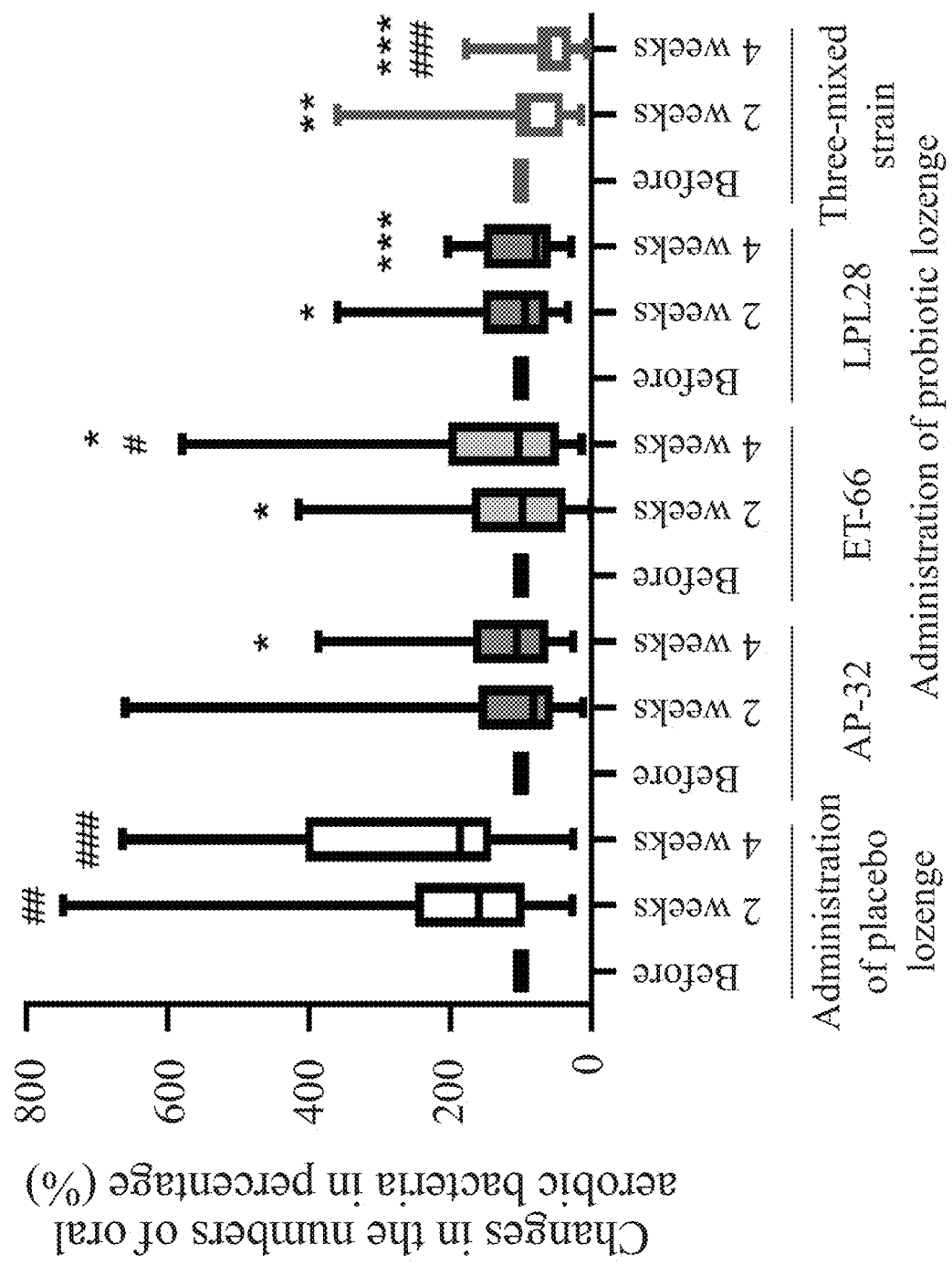
FIGS. 4A to 4D are bar charts showing the changes in the numbers of the oral anaerobic bacteria (FIG. 4A), *Streptococcus mutans* (FIG. 4B), *Bifidobacterium* spp.

As shown in FIG. 4A, the changes in the numbers of the oral aerobic bacteria in percentage significantly decreased 2 weeks after the subjects were administered with the probiotic lozenges compared to that of the subjects administered with the placebo lozenge or that of the subjects before the administration. Moreover, the effect of the three mixed-strain probiotic lozenge on decreasing the numbers of oral aerobic bacteria was better than that of the probiotic lozenges of strains AP-32, ET-66 and LPL28.

Figure 4B:
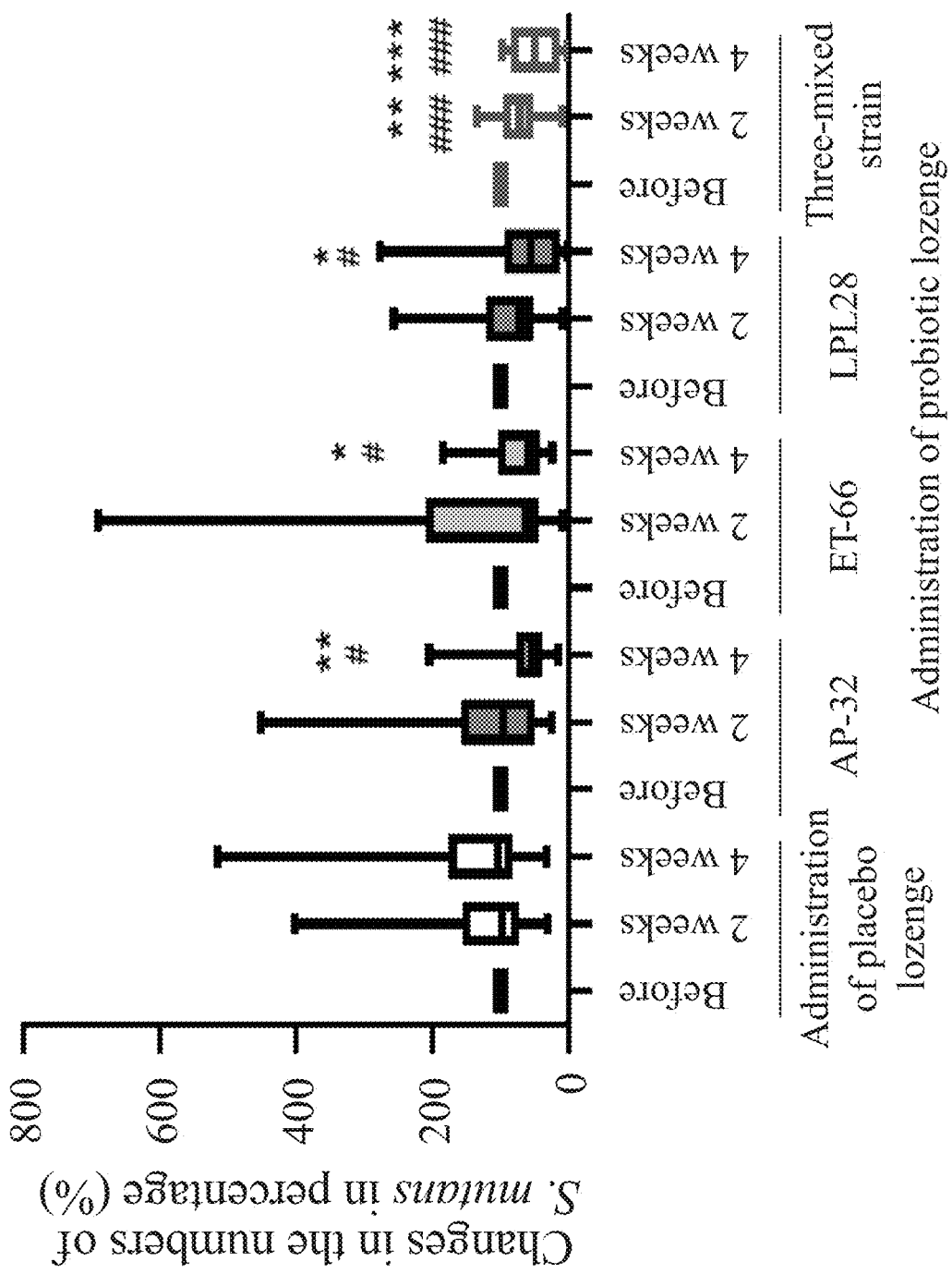

As shown in FIG. 4B, the changes in the numbers of S. mutans in percentage significantly decreased 2 weeks after the subjects were administered with the probiotic lozenges compared to that of the subject administered with the placebo lozenge or that of the subjects before the administration. Moreover, the effect of the three mixed-strain probiotic lozenge on decreasing the numbers of S. mutans was better than that of the probiotic lozenges of strains AP-32, ET-66 and LPL28.

Figure 4C:
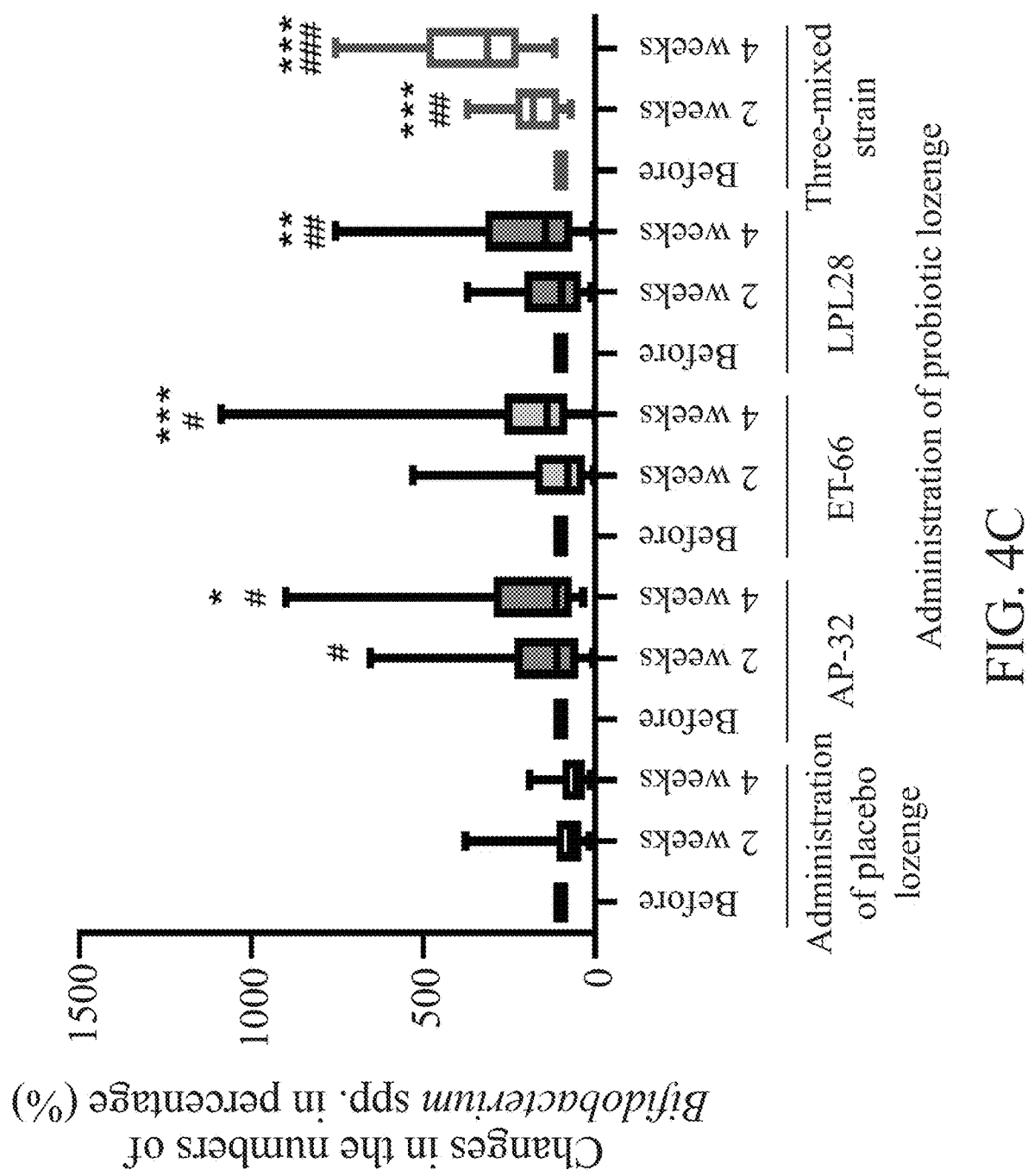

As shown in FIG. 4C, the changes in the numbers of Bifidobacterium spp. in percentage significantly increased 2 weeks after the subjects were administered with the probiotic lozenges compared to that of the subjects administered with the placebo lozenge or that of the subjects before the administration. Moreover, the effect of the three mixed-strain probiotic lozenge on increasing the numbers of Bifidobacterium spp. was better than that of the probiotic lozenges of strains AP-32, ET-66 and LPL28.

Figure 4D:
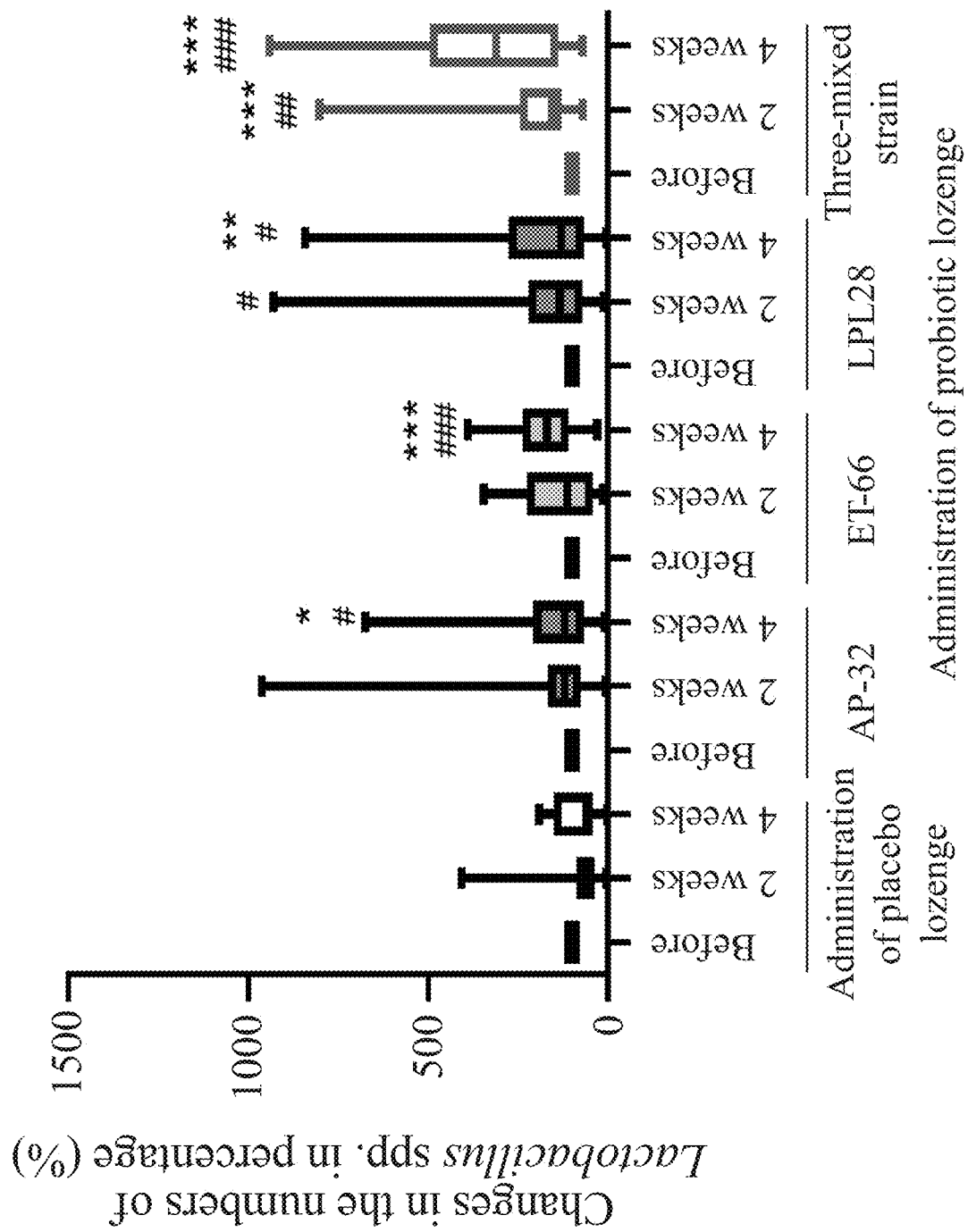

As shown in FIG. 4D, the changes in the numbers of Lactobacillus spp. in percentage significantly increased 4 weeks after the subjects were administered with the probiotic lozenges compared to that of the subjects administered with the placebo lozenge or that of the subjects before the administration. Moreover, the effect of the three mixed-strain probiotic lozenge on increasing the numbers of Lactobacillus spp. was better than that of the probiotic lozenges of AP-32, ET-66 and LPL28. Accordingly, administering the probiotic lozenges could effectively decrease the numbers of oral pathogens such as S. mutans, and effectively increase the numbers of oral probiotics such as Bifidobacterium spp. and Lactobacillus spp. In addition, the three mixed-strain probiotic lozenge had a better effect compared to that of the probiotic lozenges of the single-strain AP-32, ET-66 and LPL28.

Besides, the subjects' salivary samples were collected before the lozenge were administered, 2 weeks or 4 weeks after the lozenge were administered, followed by a DNA extract and a next generation sequencing (NGS) by BIOTOOLS CO., LTD., Taipei, Taiwan. The NGS was performed in the following steps: first, commercial primers (such as primers having the sequences shown in SEQ ID NOs: 4 to 5) and commercial PCR kits (Phusion® High-Fidelity PCR Master Mix, made by New England Biolabs, USA) were used to amplified the nucleic acid fragments of the V3 and V4 regions of 16 s rRNA, followed by an electrophoresis and a purification to obtain nucleic acid fragments with 400 bp to 450 bp, in which purification was performed with the extracting kit (Qiagen Gel Extraction kit made by Qiagen, Hilden, German).

Next, the sequencing samples were prepared by using a kit for preparing whole genomic sequencing samples (TruSeq® DNA PCR-free sample preparation kit, made by Illumina, CA, USA) to build a genomic DNA library. Then, the genomic DNA library were analyzed by a fluorescent detection device (Qubit 2.0 Fluorometer made by Thermo Fisher Scientific, MA, USA) and a system for sequence analysis (Agilent Bioanalyzer 2100 system made by Agilent Technologies, Inc., CA, USA). Subsequently, the sequences analysis was performed on the platform Illumina HiSeq 250. The NGS results were recorded in FIGS. 5A to 5B.

Figure 5A:
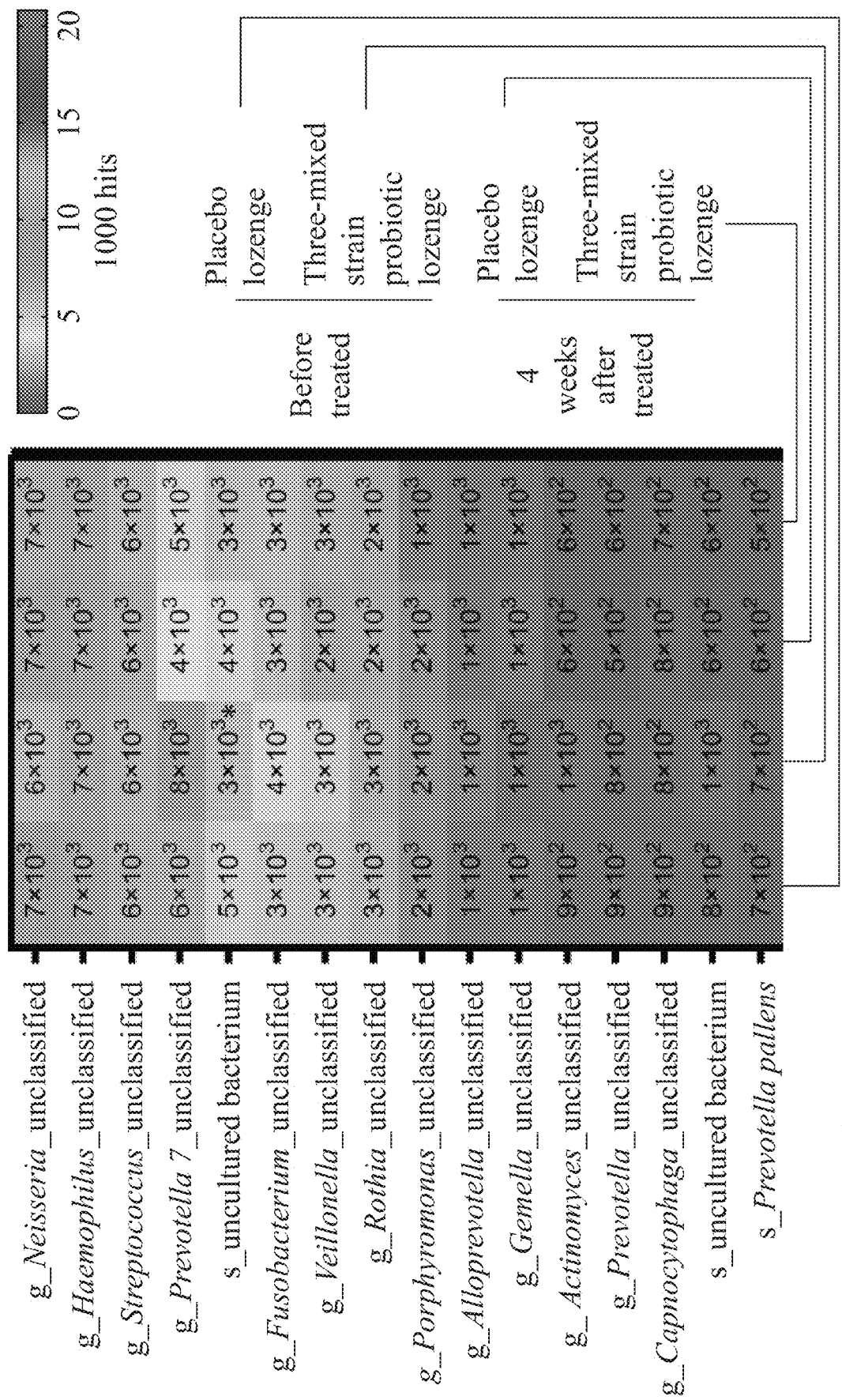
FIGS. 5A to 5B are the NGS heat maps showing the changes of the oral flora after administered with the three mixed-strain probiotic lozenge according to an embodiment of the present invention.
Figure 5B:
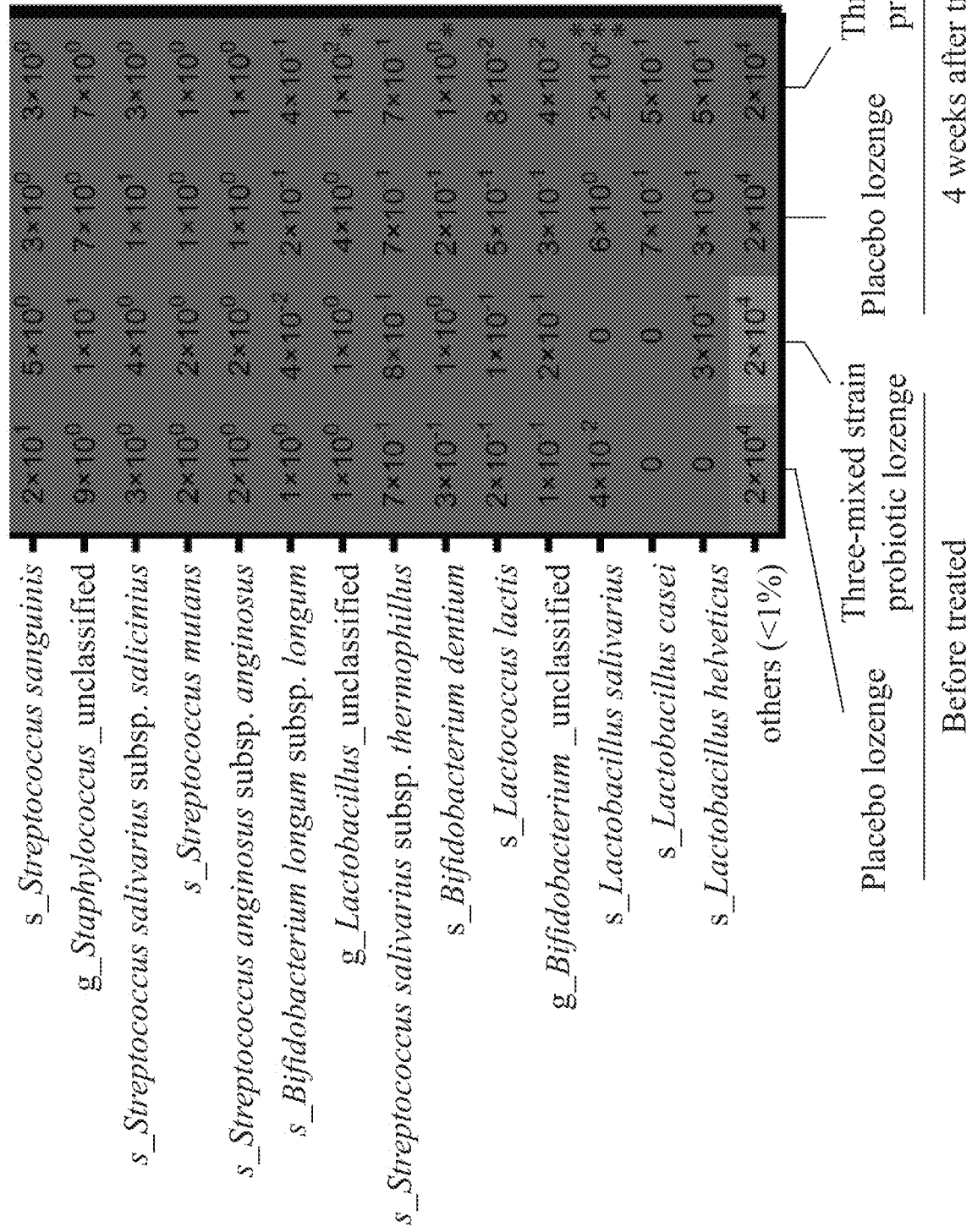

FIGS. 5A to 5B were the NGS heat maps showing the changes of the oral flora after administered with the three mixed-strain probiotic lozenge according to an embodiment of the present invention, in which the x-axis represented the categories (e.g., genus, species of subspecies) of the bacteria and the symbols "*" and "***" represented statistically significant differences against the cell amount in the mouth administered with placebo lozenge (p<0.05 and p<0.001, respectively) (n=25) analyzed by Student's t-test. As shown in FIGS. 5A to 5B, the amounts of oral probiotics (such as *L. salivarius, Lactobacillus* spp. and *Bifidobacterium dentium*) could increase effectively 4 weeks after the administration of the three mixed-strain probiotic lozenge.

Moreover, the subjects' oral and physical conditions were surveyed with a questionnaire, and the results were listed in Tables 6 and 7, respectively, in which the scores 0, 1, 2 and 3 represented no symptom, mild symptom, moderate symptom and severe symptom (in Table 7, scores 2, 1 and 0 represented one bowel movement for over 3 days, one bowel movement for 1 to 3 days and more than one bowel movement for one day, respectively) and the alphabets "a" and "b" represented statistically significant differences between the scores of the subjects administered with the probiotic lozenges and that of the subjects administered with the placebo lozenges analyzed by Student t-test. As shown in Table 6, the scores of symptoms of the subject administered with three mixed-strain probiotic lozenges like aphthae (also called canker sores or mouth sores), pustule, or drooling etc., significantly decreased. Moreover, as shown in Table 7, symptoms such as constipation, gastroesophageal reflux, colds and drowsiness were significantly improved, indicating that the three mixed-strain probiotic lozenges could not only improved oral discomfort symptoms but also assert positive effects on physical conditions besides that in a mouth.

Example 7

Evaluation of Activities of Single-Strain and Three Mixed-Strain Probiotic Lozenges to Enhance Concentration of Oral IgA Lozenges of strains AP-32, ET-66 and LPL28 were prepare by using the single-strain fermented products of the strains AP-32, ET-66 and LPL28 in EXAMPLE 4, in which the cell amounts were 50 mg/g in each lozenge. The placebo lozenge, the lozenges of strains AP-32, ET-66 and LPL28 as well as the three mixed-strain probiotic lozenge were administered to the subjects. The subjects' salivary samples were collected before the administration as well as 2 and 4 weeks after the administration, followed by an enzyme-linked immunosorbent assay (ELISA) to determine the amounts of IgA of the subjects, and the results were recorded in FIG. 6. The method of ELISA was a common general knowledge to persons skilled in the art and would not be elaborated herein.

Figure 6:
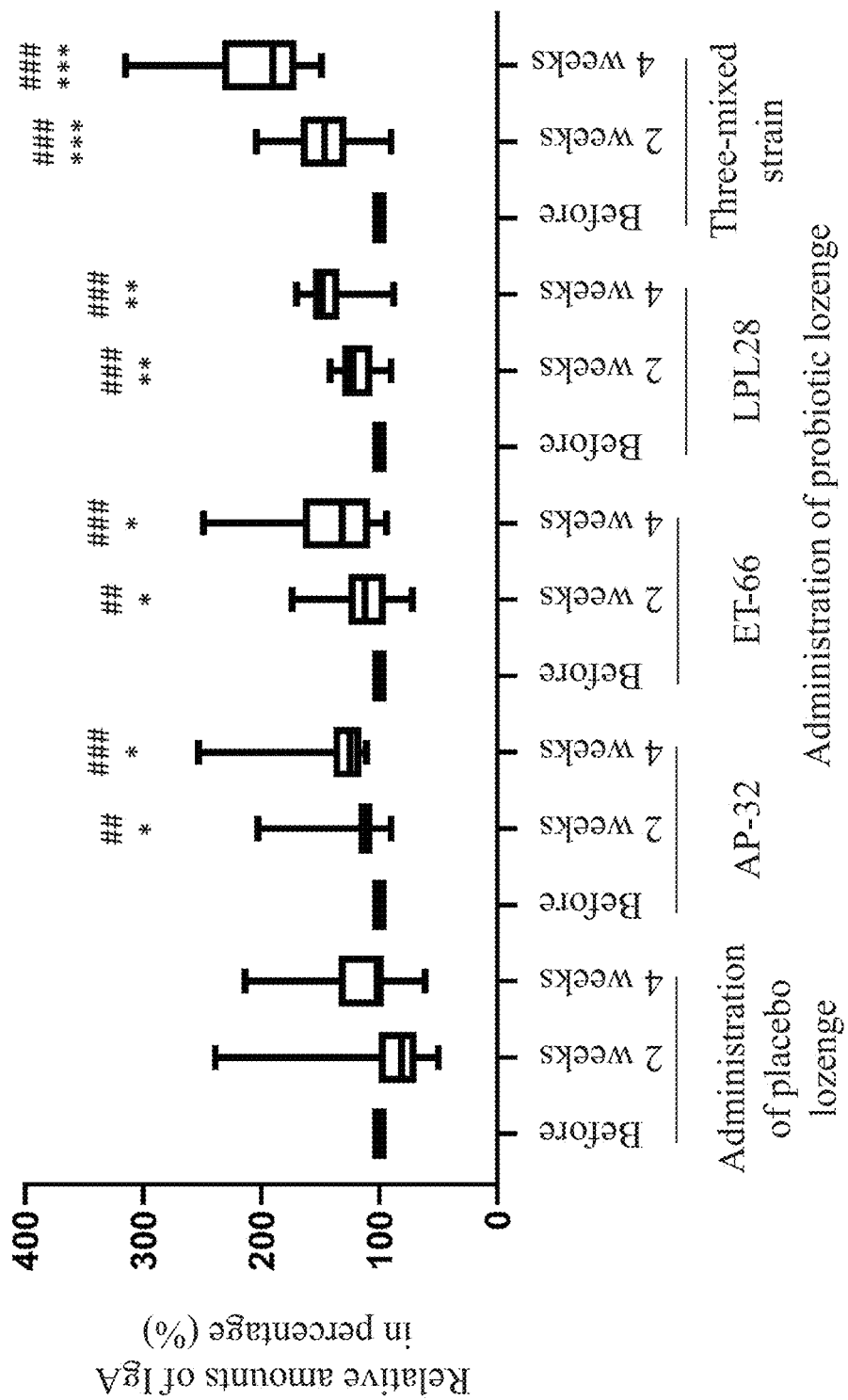
FIG. 6 is a box plot showing the relative amounts of IgA in percentage before or different times after administered with different lozenges according to an embodiment of the present invention.

FIG. 6 was a box plot showing the relative amounts of IgA in percentage before or different times after administered with different lozenges according to an embodiment of the present invention, in which the x-axis represented the types of lozenges and timing, the y-axis represented the relative amounts of IgA in percentage taking the amounts of IgA before the administration as 100%, symbols "*", "" and "*" represented statistically significant differences in the amounts of IgA of the subjects administered with the placebo lozenges (p<0.05, p<0.01 and p<0.001, respectively) analyzed by Student t-test, and symbols "##" and "###" represented a statistically significant difference in the relative amounts of IgA of the subjects before the administration (p<0.01 and p<0.001, respectively) (n=25) analyzed by Student t-test.

TABLE 6

| | Placebo lozenges administration | | | Three-mixed strain probiotic lozenges administration | | |
|---|---|---|---|---|---|---|
| | before | 2 weeks after | 4 weeks after | before | 2 weeks after | 4 weeks after |
| Toothache/swollen gums | 0.4 ± 0.71 | 0.2 ± 0.41 | 0.16 ± 0.47 | 0.48 ± 0.59 | 0.28 ± 0.54 | 0.16 ± 0.37 |
| Teeth bleeds when brushing | 0.48 ± 0.78 | 0.44 ± 0.65 | 0.44 ± 0.65 | 0.44 ± 0.58 | 0.28 ± 0.61 | 0.16 ± 0.37 |
| Mouth sores or pustules | 0.6 ± 0.76 | 0.72 ± 0.98 | 0.52 ± 0.82 | 0.44 ± 0.82 | 0.04 ± 0.2b | 0.08 ± 0.28a |
| Sore throat | 0.48 ± 0.59 | 0.4 ± 0.87 | 0.36 ± 0.76 | 0.28 ± 0.46 | 0.2 ± 0.41 | 0.16 ± 0.47 |
| Drooling | 0.32 ± 0.56 | 0.52 ± 0.82 | 0.48 ± 0.65 | 0.6 ± 0.76 | 0.12 ± 0.33a | 0.16 ± 0.37a |
| Cough | 0.32 ± 0.48 | 0.24 ± 0.6 | 0.4 ± 0.76 | 0.36 ± 0.57 | 0.12 ± 0.44 | 0.12 ± 0.44 |

TABLE 7

| | Placebo lozenges administration | | | Three-mixed strain probiotic lozenges administration | | |
|---|---|---|---|---|---|---|
| | before | 2 weeks after | 4 weeks after | before | 2 weeks after | 4 weeks after |
| bowel movement | 0.08 ± 0.28 | 0.2 ± 0.41 | 0.36 ± 0.49 | 0.2 ± 0.41 | 0.4 ± 0.5 | 0.32 ± 0.48 |
| constipation | 0.48 ± 0.65 | 0.44 ± 0.65 | 0.6 ± 0.71 | 0.28 ± 0.46 | 0.16 ± 0.37 | 0.12 ± 0.33$^b$ |
| diarrhea | 0.2 ± 0.41 | 0.32 ± 0.63 | 0.36 ± 0.64 | 0.12 ± 0.33 | 0.24 ± 0.66 | 0.16 ± 0.37 |
| stomachache | 0.68 ± 0.8 | 0.4 ± 0.65 | 0.32 ± 0.63 | 0.36 ± 0.49 | 0.12 ± 0.33 | 0.16 ± 0.37 |
| gastro-esophageal reflux | 0.68 ± 0.9 | 0.48 ± 0.65 | 0.52 ± 0.71 | 0.28 ± 0.46 | 0.08 ± 0.28$^b$ | 0.12 ± 0.33$^a$ |
| cold | 0.36 ± 0.57 | 0.44 ± 0.71 | 0.56 ± 0.82 | 0.32 ± 0.47 | 0.2 ± 0.41 | 0.16 ± 0.37$^a$ |
| drowsiness | 0.36 ± 0.7 | 0.4 ± 0.58 | 0.52 ± 0.65 | 0.32 ± 0.56 | 0.16 ± 0.37 | 0.12 ± 0.33$^b$ |

As shown in FIG. 6, the relative amounts of salivary IgA of the subjects administered with the AP-32 lozenge, the ET-66 lozenge, the LPL28 lozenge and the three mixed-strain probiotic lozenge increased 2 weeks and 4 weeks after the administration, indicating that the strains AP-32, ET-66 and LPL28 could increase the amounts of salivary IgA. However, the relative amounts of salivary IgA of the subjects administered with the three mixed-strain probiotic lozenges were higher than that of the subjects administered with the AP-32 lozenge, the ET-66 lozenge and the LPL28 lozenge, indicating that the three mixed-strain fermented product could increase more amounts of salivary IgA compared to the strains AP-32, ET-66 and LPL28.

Example 8

Evaluation of Amounts of IgA Increased by Three Mixed-Strain Postbiotic Lozenge

The three mixed-strain postbiotic lozenge prepared in EXAMPLE 5 was administered to the subjects for 4 weeks, in which the method of administration and the criteria of the subjects were same as EXAMPLE 6. The subjects' salivary samples were respectively collected before the administration as well as 2 and 4 weeks after the administration, followed by the aforementioned ELISA to determine the amounts of salivary IgA.

Figure 7:
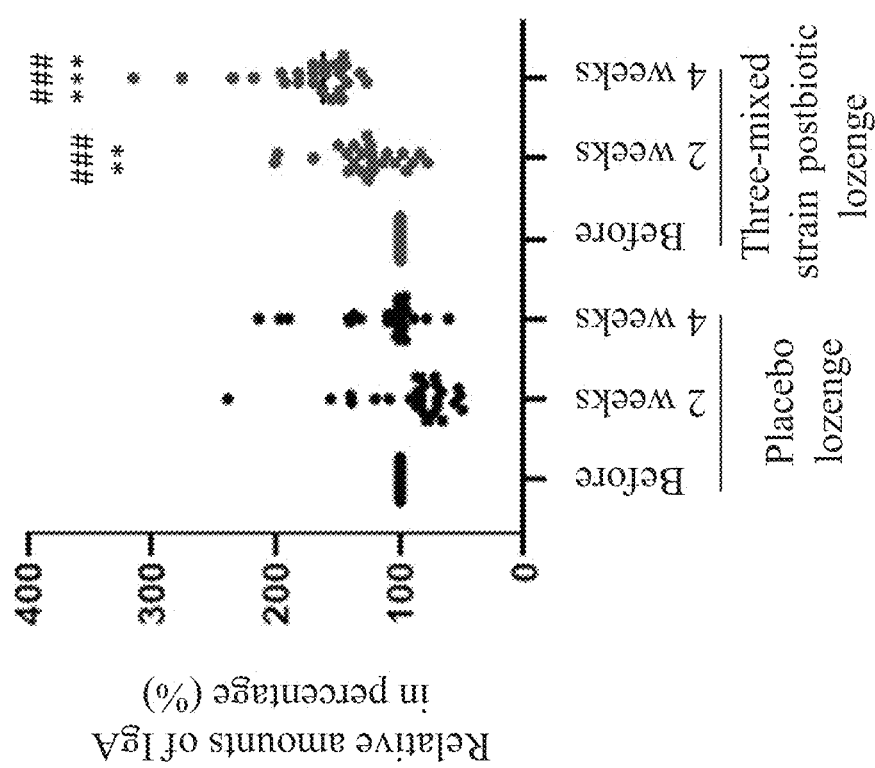
FIG. 7 is a column scatter plot showing the amount of salivary IgA in percentage at different times after administrated with three mixed-strain postbiotics lozenge according to an embodiment of the present invention.

FIG. 7 was a column scatter plot showing the amounts of salivary IgA in percentage at different times after administrated with three mixed-strain postbiotic lozenge according to an embodiment of the present invention, in which the x-axis represented the time and the types of the lozenges, the y-axis represented the amounts of salivary IgA in percentage taking the amounts of salivary IgA of the subjects before the administration as 100%, symbols "" and "*" represented statistically significant differences in the amounts of IgA of the subjects administered with the placebo lozenges ($p<0.01$ and $p<0.001$, respectively) (n=25) analyzed by Student t-test, and the symbols "###" represented a statistically significant difference in the amounts of IgA of the subjects before administered with the three mixed-strain postbiotic lozenge ($p<0.001$) (n=25) analyzed by Student t-test. As shown in FIG. 7, the amounts of salivary IgA of the subjects administered with the three mixed-strain postbiotic lozenge increased after 2 and 4 weeks, indicating that the three mixed-strain postbiotic lozenge of the strains AP-32, ET-66 and LPL28 could effectively increase the amounts of salivary IgA.

The abovementioned results showed that the *L. plantarum* LPL28 of the present invention could exactly increase the amounts of IgA and inhibit the oral pathogens, suggesting that the application of the *L. plantarum* LPL28 of the present invention could decrease the incidence rate of caries and/or periodontitis, and thus having the potential to prevent caries and/or periodontitis.

In sum, although specific strains, specific dosage form, specific subjects, specific method of administration or specific evaluation methods are shown in the present invention as examples to explain the method of increasing an amount of oral IgA in a subject in need thereof, in which the method includes administering a therapeutically effective amount of a composition including probiotics (such as *L. plantarum* LPL28) as an active ingredient to the subject, it will be apparent to those skilled in the art that the present invention is not limited to what have mentioned. Without departing from the scope or spirit of the invention, it is intended that other strains, other dosage forms, other subjects, other methods of administration or other evaluation methods can also explain the present invention.

Although the present invention has been described in considerable detail with reference to certain embodiments thereof, other embodiments are possible. Therefore, the spirit and scope of the appended claims should not be limited to the description of the embodiments contained herein.

What is claimed is:

1. A method of increasing an amount of oral immunoglobulin A (IgA) in a subject in need thereof, comprising:
administering a therapeutically effective amount of a composition comprising probiotics as an active ingredient to the subject, wherein the probiotics comprise *Lactobacillus plantarum* LPL28 that is deposited at China General Microbiological Culture Collection Center (CGMCC) under an accession number of CGMCC 17954.

2. The method of increasing the amount of oral IgA in the subject in need thereof of claim 1, wherein the probiotics further comprise *L. salivarius* AP-32 and/or *L. paracasei* ET-66, the *L. salivarius* AP-32 is deposited in China Center for Type Culture Collection (CCTCC) under accession number CCTCC M 2011127, and the *L. paracasei* ET-66 is deposited in CGMCC under accession number.

3. The method of increasing the amount of oral IgA in the subject in need thereof of claim 1, wherein the composition is a food composition or an oral topical composition.

4. The method of increasing the amount of oral IgA in the subject in need thereof of claim 3, wherein the food composition is a dairy product, a non-dairy beverage, or an oral cleansing food.

5. The method of increasing the amount of oral IgA in the subject in need thereof of claim 3, wherein the oral topical composition is an oral care composition or a breath freshening composition.

6. The method of increasing the amount of oral IgA in the subject in need thereof of claim 1, wherein the probiotics are subjected to a heat-kill step.

7. The method of increasing the amount of oral IgA in the subject in need thereof of claim 1, wherein the probiotics are subjected to a heat-kill step and a centrifuge step.

8. A method of increasing an amount of IgA in a subject in need thereof, comprising:
administering a therapeutically effective amount of a composition comprising probiotics as an active ingredient to the subject, wherein the probiotics comprise *L. plantarum* LPL28 under an accession number of CGMCC 17954, *L. salivarius* AP-32 under an accession number of CCTCC M 2011127 and *L. paracasei* ET-66 under an accession number of CGMCC 13514.

9. The method of increasing an amount of IgA in the subject in need thereof of claim 8, wherein the composition is a food composition or an oral topical composition.

10. The method of increasing an amount of IgA in the subject in need thereof of claim 9, wherein the food composition is a dairy product, a non-dairy beverage, or an oral cleansing food.

11. The method of increasing an amount of IgA in the subject in need thereof of claim 9, wherein the oral topical composition is an oral care composition or a breath freshening composition.

* * * * *

SEQUENCE LISTING

<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: forward primer for 16S rRNA gene

<400> SEQUENCE: 1
cgatcgtggg actgttaagg                    20

<210> SEQ ID NO 2
<211> LENGTH: 20
<212> TYPE: DNA
<213> ORGANISM: Artificial Sequence
<220> FEATURE:
<223> OTHER INFORMATION: reverse primer for 16S rRNA gene

<400> SEQUENCE: 2
cacgtaataa cgcaccaacg                    20

<210> SEQ ID NO 3
<211> LENGTH: 145
<212> TYPE: DNA
<213> ORGANISM: Unknown
<220> FEATURE:

```
<223> OTHER INFORMATION: partial sequence of 16S rRNA gene of
      Lactobacillus plantarum LPL28

<400> SEQUENCE: 3
ccatagcgtg taatgagtca accgccgtct tagtagcttc ttcaatccca cgacgaatgc      60
caacagggtt agcaccggcc gtaacgttct tcataccttc attaacgatt gattgtgtta     120
agaccgttgc agtagtcgtc ccatc                                           145

<210> SEQ ID NO 4
<211> LENGTH: 17
<212> TYPE: DNA
<213> ORGANISM: Artificial Sequence
<220> FEATURE:
<223> OTHER INFORMATION: forward primer for NGS
<220> FEATURE:
<221> NAME/KEY: misc_feature
<222> LOCATION: (9)..(9)
<223> OTHER INFORMATION: n is a, c, g, or t

<400> SEQUENCE: 4
cctacgggng gcwgcag                                                     17

<210> SEQ ID NO 5
<211> LENGTH: 21
<212> TYPE: DNA
<213> ORGANISM: Artificial Sequence
<220> FEATURE:
<223> OTHER INFORMATION: reverse primer for NGS

<400> SEQUENCE: 5
gactachvgg gtatctaatc c                                                21
```